United States Patent [19]

Smith

[11] Patent Number: 4,925,866

[45] Date of Patent: May 15, 1990

[54] METHOD FOR CONTROLLING PLANT DISEASES AND MICROOGANISMS IN THE PRESENCE OF PLANTS

[75] Inventor: Roger E. Smith, West Lafayette, Ind.

[73] Assignee: Great Lakes Chemical Corporation, West Lafayette, Ind.

[21] Appl. No.: 378,150

[22] Filed: Jul. 11, 1989

Related U.S. Application Data

[63] Continuation of Ser. No. 278,722, Dec. 2, 1988, abandoned, which is a continuation of Ser. No. 925,321, Oct. 31, 1986, abandoned.

[51] Int. Cl.$^5$ ............................................. A01N 43/50
[52] U.S. Cl. ........................................ 514/389; 71/31; 71/67
[58] Field of Search ........................ 514/389; 71/3, 67

[56] References Cited

U.S. PATENT DOCUMENTS

| | | | |
|---|---|---|---|
| 3,412,021 | 11/1968 | Paterson | 514/389 |
| 4,058,618 | 11/1977 | Orchinnikov et al. | 514/389 |
| 4,167,832 | 9/1979 | Zefferquist et al. | 47/1 R |
| 4,198,423 | 4/1980 | Rentzea et al. | 548/311 |
| 4,454,133 | 6/1984 | Berke et al. | 514/389 |
| 4,655,815 | 4/1987 | Jakubowski | 71/67 |

*Primary Examiner*—John W. Rollins

*Attorney, Agent, or Firm*—Senniger, Powers, Leavitt and Roedel

[57] ABSTRACT

The present invention is directed to a novel method for controlling the growth of microorganisms on, in or near plants. more particularly, in one embodiment, growth of microorganisms is controlled on a surface that is in such proximity to a higher order plant that contacting such surface with a stream of water may cause liquid water from the stream to be deflected and contact the higher order plant or the growth medium in which it is rooted. In this embodiment, an N-halohydantoin is incorporated in water to produce treated water havng an N-halohydantoin concentration sufficient to inhibit the growth of microorganisms in the water or on a substrate to which the treated water is applied. Then the surface is contacted with the treated water, thereby inhibiting the growth of microorganisms on the surface, without harming the higher order plant by contact with the N-halohydantoin contained in any of the treated water that may contact the plant or the growth medium in which said plant is rooted. In other embodiments, plants fruit, vegetables, seeds, plant bulbs, or the medium in which plants, seeds or bulbs are implanted may be treated with N-halohydantoin to control plant disease or unwanted microorganisms without harming the plants, fruit, seeds or plant bulbs.

28 Claims, No Drawings

METHOD FOR CONTROLLING PLANT DISEASES AND MICROOGANISMS IN THE PRESENCE OF PLANTS

This is a continuation of Ser. No. 278,722, filed 12/2/88, now abandoned, which is a continutation of Ser. No. 925,321, filed 10/31/86, now abandoned.

BACKGROUND OF THE INVENTION

This invention relates to plant diseases and deleterious microorganisms found in environments adapted for the growth of higher order plants, and more particularly to control and inhibition of plant diseases and deleterious microorganisms found in such environments.

In environments adapted for the growth of plants of higher biological development or complexity than microorganisms such as bacteria, yeast, algae or simple fungus, that is, in environments adapted for the growth of higher order plants, development of such microorganisms on practically any moist surface has been a longstanding and intractable problem.

Greenhouses contain a myriad of water sources, including irrigation water, irrigation water run-off, spilled water, cleaning water, condensation, atomized water drifting from a humidifier or evaporative cooler and extraneous sprayed water as might result from a water hose. Since almost all surfaces in a greenhouse tend to become moist from these sources, nearly any surface in a greenhouse may serve as a site for microorganism growth. Thus, in conventional greenhouses, microorganisms inevitably colonize and grow not only on the plants themselves, but also on all other surfaces such as walls, ceilings, floors, flower pots, flats, irrigation mats, irrigation equipment and evaporative cooling pads.

Similarly, in outdoor nurseries, crop fields, and any other environment, such as lawns or golf courses, adapted for the growth of higher order plants, microorganisms tend to develop on irrigation or sprinkling equipment, soil and the plants themselves, and containers and planters.

Growth of microorganisms often is deleterious to the operation of an irrigation system as well as to the higher order plants themselves. Growth of slime bacteria has a propensity to foul the system and clog irrigation equipment, reducing its efficiency. Likewise, development of yeast, fungus and algae causes spoiling of plants, and the fruits and seeds of plants, and otherwise harms higher order plants. Development of pathogenic microorganisms such as Verticillium, Pythium, Fusarium, and Pseudomonas in or on plants also causes various plant diseases. Furthermore, microorganism development in living plants may accelerate rotting or spoiling of the plants after harvesting, or even accelerate rotting or spoiling of fruits or seeds harvested from the plants. Moreover, development of microorganisms in a greenhouse can cover the greenhouse with an unappealing slime which rubs off on workers who brush against a coated greenhouse surface, blocks light transmission through the glass walls of the greenhouse, fouls the greenhouse, makes the greenhouse floors slippery, provide a breeding ground for fungus gnats and other pests, and potentially poses health hazards.

Previous attempts to inhibit microorganism development in plant environments either have failed or have been self-defeating because ordinary biocides or disinfectants, such as bleach or various quaternary ammonium compounds, that have been employed to kill or inhibit microorganisms, also are toxic to the higher order plants in the environment. Thus, ordinarily the cleaning of greenhouse surfaces has entailed tedious, labor intensive careful scrubbing of the surfaces to avoid accidentally contacting a plant with the biocide, or time consuming removal of all the higher order plants from the greenhouse before washing down the surfaces with a hose. Moreover, it seems clear that because such biocides are phytotoxic, they cannot be considered for direct plant treatment either in the irrigation water to keep clean the surfaces contacted by the water, or in irrigation water or otherwise in order to treat the plants themselves. On the other hand, however, while some biocides may have low enough phytotoxic characteristics to use directly on plants, many have been associated with health hazards to humans that eat the plants or harvested parts thereof.

In addition to the health hazards from the toxicity of the oxidizing biocides used in the prior art for treating microorganism development around plants, such biocides also usually involve other health hazards from some other characteristic, such as the explosiveness of chlorine gas tanks. Other problems with many of the conventional chlorine biocides include instability of the biocide in the presence of organic matter, effectiveness of the biocide only in a narrow pH range, and the formation of chloramines in the presence of ammonia, thereby producing residual compounds which undesireably persist in the environment. Further, the additives typically employed in irrigation systems for control of certain microorganisms, or for other purposes such as fertilization, tend to be compositions of high water solubility and so require employment of expensive pumps and other mechanical parts to regulate the concentration of the additives, to maintain an appropriate concentration and to avoid a phytotoxic overdose.

As disclosed in Paterson U.S. Pat. No. 3,412,021 and Macchiarolo U.S. Pat. No.4,297,224, 1-bromo-3- chloro-5,5-dimethylhydantoin is known as an oxidizing biocide for use in water treatment in certain environments, such as swimming pools and cooling towers in which higher order plants are not a concern. Patent and other technical literature discloses a number of uses for this and other N-halohydantoin compounds based on the biocidal properties of these compounds.

SUMMARY OF THE INVENTION

Among the several objects of the invention, therefore, may be noted the provision of a method for controlling unwanted microorganisms located on, in or near higher order plants without harming the higher order plants; the provision of a method for cleaning greenhouses and surfaces therein with biocide treated water that does not harm higher order plants; the provision of a method for treating higher order plants for inhibition of unwanted microorganisms without harming the higher order plants; the provision of a method for treating higher order plants for controlling disease to the plants without harming the plants; the provision of a method for treating higher order plants for inhibition of unwanted microorganisms and control of disease without harm to the plants and without the need for extra pumps to apply the treatment; the provision of a method for treating harvested plants, fruits, vegetables, and seeds for inhibition of rotting or spoiling by treating growing plants; the provision of a method for irrigating plants whereby development of unwanted microorganisms is inhibited; the provision of a method for treating soil, growth media or aggregate, or hydroponic solutions for inhibiting unwanted microorganisms without harming the plants; the provision of a method for treating an evaporative cooler or humidifier whereby development of unwanted microorganisms is inhibited; and the provision of a method for treating an evaporative cooler or humidifier whereby development of unwanted microorganisms is inhibited, and plants contacted by atomized water emitted from the evaporative cooler or humidifier are unharmed.

Briefly, therefore, the present invention is directed to a novel method for controlling the growth of microorganisms on a surface that is in such proximity to a higher order plant that contacting such surface with a stream of water may cause liquid water from the stream to be deflected and contact the higher order plant or the growth medium in which it is rooted. Also controls microorganisms in the root zone within the growth media. The method comprises incorporating an N-halohydantoin in water to produce treated water having an N-halohydantoin concentration sufficient to inhibit the growth of microorganisms in the water or on a substrate to which the treated water is applied, and contacting the surface with the treated water, thereby inhibiting the growth of microorganisms on the surface. In the method, the higher order plant remains unharmed by the N-halohydantoin contained in any of the treated water that that may contact the plant or the growth medium in which the plant is rooted.

The present invention is also directed to a novel method for controlling growth of unwanted microorganisms on a surface whereby a higher order plant is not harmed, the surface being located in an environment for the growth of a higher order plant. The method comprises incorporating N-halohydantoin in water to produce treated water having a concentration of N-halohydantoin sufficient to inhibit growth of microorganisms, and contacting a surface with the treated water for controlling microorganisms thereon, the higher order plant being contacted with the treated water in connection with contacting the surface with the treated water.

The present invention is further directed to a novel method for irrigating plants wherein growth of unwanted microorganisms on or in the plants is controlled without harming the plants. The method comprises incorporating N-halohydantoin in water to produce treated water having a concentration of N-halohydantoin sufficient to inhibit growth of microorganisms, and irrigating plants with the treated water. The present invention is also directed to such irrigation methods in which growth of unwanted microorganisms in or on irrigation equipment and materials is controlled, and to such methods in which plant disease is controlled without harming the plants.

The present invention is further directed to a novel method for controlling growth of disease or unwanted microorganisms in a plant or a plant rhizosphere without harming the plant. The method comprises applying an N-halohydantoin to a growth medium in which the plant is rooted. The N-halohydantoin is dissolved in and conveyed to the rhizosphere by precipitation or irrigation water received by the growth medium. The invention is also directed to such method wherein the N-halohydantoin is applied to a growth medium in which a seed or bulb for the plant are implanted.

The present invention is also drawn to a novel method for controlling disease or growth of unwanted microorganisms in or on a plant without harming the plant. The method comprises contacting the plant with an N-halohydantoin, preferably by dissolving N-halohydantoin in water to produce a disinfectant solution having a concentration of N-halohydantoin sufficient to inhibit growth of microorganisms, and applying the disinfectant solution to said plant. Alternatively, a seed or bulb for the plants may be treated with N-halohydantoin.

The present invention is also drawn to a novel method for treating harvested plants whereby growth of unwanted microorganisms in or on the harvested plants is controlled without harming the plants. In the method, harvested plants are contacted with an N-halohydantoin. Preferably, N-halohydantoin is dissolved in water to produce a disinfectant solution having a concentration of N-halohydantoin sufficient to inhibit growth of microorganisms. Then, the harvested plants are contacted with the disinfectant solution, whereby rotting or spoiling of the harvested plants is inhibited.

The present invention is further drawn to a novel method for production of harvested plants, fruit or seeds, or controlling disease in the plants, fruits, seeds, or vegetables, whereby growth of unwanted microorganisms in or on the vegetables, plants, fruit or seeds is controlled without harm to the vegetables, plants, fruit or seeds. In the method, growing plants are contacted with an N-halohydantoin and then the plants, or fruit or seeds from the plant are harvested. Preferably, the method comprises several steps. First, N-halohydantoin is dissolved in water to produce a disinfectant solution having a concentration of N-halohydantoin sufficient to inhibit growth of microorganisms. Then, growing plants are contacted with the disinfectant solution. Finally, the growing plants, or their fruit or seeds are harvested and rotting or spoiling of the harvested plants is inhibited.

DESCRIPTION OF THE PREFERRED EMBODIMENT

In accordance with the present invention, it has been discovered that N-halohydantoins, their metabolites and residuals, can be used for effective control of microorganisms in a plant environment without risk of injury to higher order plants. More particularly it has ben found that aqueous solutions of N-halohydantoins may be formulated in a wide easily attainable range of concentrations that are high enough to kill various unwanted microorganisms such as slime bacteria, yeast, fungus and algae, yet low enough not to harm higher order plants, whether contact of the plant with the solution is intentional or incidental. Regulation of the concentration of N-halohydantoin is simplified by the relatively low solubility of these compounds in water, and the fact that the highest concentration of N-halohydantoin that is obtained under ordinary conditions is too low to result in phytotoxicity. Unexpectedly, not only is a saturated solution of N-halohydantoin harmless to plants but, astonishingly, actually seems to stimulate plant growth. It has further been found that solid state N-halohydantoins are not harmful to higher order plants, and that these biocides may thus be applied in either solid or solution form in plant environments, or indeed to the plants thermselves, without risk of injury to plant systems or tissue.

Moreover, since ingestion of reasonable amounts of N-halohydantoins is not believed to pose health dangers to humans from toxicity, ingestion of plants or parts thereof treated with N-halohydantoin is believed to present no serious or appreciable health risk. Further, since N-halohydantoins are neither flammable nor typically stored in pressurized containers, they do not present dangers from explosions. The N-halohydantoins of this invention also show greater stability in the presence of organic matter and effectiveness over a wider pH range than shown by typical chlorine disinfectants of the prior art. Further, the N-halohydantoins of this invention do not tend to form chloramines in the presence of ammonia, and so are not believed to form residual compounds which undesirably persist remain in the environment.

Due to the surprising selective toxicity of aqueous N-halohydantoin compositions, the compositions can be employed in many biocidal applications wherein the composition does or may contact desired higher order plants. Accordingly, greenhouse surfaces susceptible to microorganism development may be cleaned with a solution of N-halohydantoin without undue concern as to whether any of the solution incidentally contacts the higher order plants growing in the greenhouse. Moreover, N-halohydantoin can be incorporated into irrigation water to control the growth of microorganisms in the water, on the irrigation equipment and on surfaces contacted by the water without harming the plants to be irrigated.

It has also been found that because of the selective phytotoxicity characteristic, N-halohydantoin can be incorporated into irrigation water or otherwise applied directly to plants or to the growth medium in which plants are rooted to treat the plants, to control microorganism development in, on and around the plants and to control certain plant diseases, without harming the plants. Also surprisingly, it has been discovered that treating growing plants with N-halohydantoin and then harvesting the plants, or their fruit or seeds, results in harvested plants, fruit or seeds that do not rot or spoil as early as do harvested untreated plants, or fruit or seeds from untreated plants. It further has been found that the benefit of delayed rotting or spoiling also can be achieved by applying N-halohydantoin composition directly to the harvested plants, fruit and seeds.

In addition, it has been found that the relatively low water solubility of N-halohydantoins avoids the formation of a highly concentrated phytotoxic solution. However, the concentration necessary for inhibiting microorganism development is so low that the low solubility of N-halohydantoin does not present a significant obstacle to production of a solution effective in killing microorganisms. In fact, even solutions of low N-halohydantoin concentration have been found to be dramatically effective in killing microorganisms. Therefore, N-halohydantoin practically self-regulates for the appropriate concentration range, and it is essentially unnecessary to provide expensive pumps and other mechanical parts for introduction of N-halohydantoin into a water system, or to introduce the biocide in a meticulously regulated manner to carefully control the N-halohydantoin concentration therein.

It also has been found that incorporating N-halohydantoin in a circulating water system, such as an evaporative cooler or humidifier, located in a greenhouse or otherwise located in Close proximity to desired plants or other organisms keeps the system substantially free of unwanted microorganisms but does not harm the desired plants or other organisms in the environment. Moreover, it is believed that the atomized treated water propelled from the cooler or humidifier and contacting surfaces and plants and other organisms in the environment improves the sanitation of the environment.

Preferably, the N-halohydantoin of this invention is an N,N'-dihalohydantoin compound, more preferably a 1,3-dihalohydantoin corresponding to the formula:

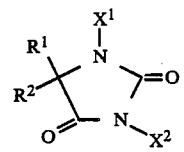

where $R^1$ and $R^2$ are independently selected from among hydrogen and alkyl, and $X^1$ and $X^2$ are independently selected from among fluorine, chlorine, bromine, and iodine. Where $R^1$ and/or $R^2$ are alkyl, they may for example, comprise methyl, ethyl, n-propyl, isopropyl, n-butyl, or n-pentyl. Generally, it is preferred that the constituents comprising $R^1$ and/or $R^2$ contain not more than about 5 carbon atoms. Preferred N-halohydantoins are N-halogenated dialkylhydantoins, especially N-halogenated dimethylhydantoins. Particularly preferred N-halohydantoins include 1,3-dibromo-5,5-dimethylhydantoin, 1-bromo-3-chloro-5,5-dimethylhydantoin, and 1,3-dichloro-5,5dimethylhydantoin, and other hydantoin derivatives.

In this invention, N-halohydantoin is incorporated in water to produce an oxidizing biocide composition. The concentration of N-halohydantoin in the composition as it is applied to inhibit microorganism development or to control plant disease should be at least about one part per million, and preferably at least about 5 ppm, to be effective against microorganisms and related diseases. However, the concentration of N-halohydantoin in the composition as the composition contacts desired higher order plants should not exceed the Point at which the composition becomes phytotoxic. Nevertheless, it has been found that the concentration of N-halohydantoin, due to its low solubility, under ordinary conditions, does not exceed about 1500 ppm, at which concentration not only has phytotoxicity not been observed, but the growth of higher order plants seems to be stimulated. Thus, a biocide of N-halohydantoin concentration between about 1 and about 1500 ppm has been found effective to kill unwanted microorganisms, yet harmless to higher order plants.

The N-halohydantoin may be incorporated into a water system at any point in the system although, of course, for a non-recirculating system the biocidal activity resulting from the N-halohydantoin only occurs downstream of the Point of incorporation. Moreover, as noted, due to the self-regulatory nature of the N-halohydantoin dissolution, special pumps and other mechanical parts for metering the N-halohydantoin are unnecessary, and so the incorporation of the N-halohydantion in water can be an essentially passive operation.

Thus, for example, solid N-halohydantoin, Preferably in particulate form, can be placed in a mesh bag and suspended in a stream of water or in a well of a water circulating system Water contacting the N-halohydantoin in the bag dissolves some of the N-halohydantoin.

For a stream the relationship between flow rate and effective area of contact between water and solid biocide should be such that the downstream: N-halohydantoin concentration is at least 1 ppm. As noted, due to the relatively low water solubility of N-halohydantoins, the concentration of N-halohydantoin under ordinary conditions remains less than about 1500 Ppm. Ordinarily, the concentration remains between 2 Ppm and 10 ppm. Preferrably the concentration is between about 5 ppm and about 10 ppm. Accordingly, by this essentially passive mechanism, the treated water contains a concentration of N-halohydantoin sufficient to control development of microorganisms and plant disease without harming higher order plants.

On the other hand, if so desired, N-halohydantoin may be introduced into the water by means of an inexpensive standard halogenator or rominator. If a brominator is used, either the entire water stream is directed through the brominator, or a side stream is diverted, passed through the brominator and reunited with the main stream. Likewise, for applications of N-halohydantoin by hose, a brominator may be connected to the hose line or N-halohydantoin may be Placed in a hose attachment such as those originally intended for application of detergents and cleaning compounds.

There are several applications for the water so treated with N-halohydantoin. For example, the treated water can be applied to an irrigation system to clean the irrigation equipment and other surfaces, to clean or to treat the plants and the fruit and seeds they bear, to treat by foliar application the plants and the fruit and seeds the plants bear, to clean a greenhouse without harming plants therein and to treat and to clean evaporative coolers or humidifiers often found in a greenhouse.

In a greenhouse, plants are often watered by means of a capillary mat irrigation system. In a capillary mat irrigation system, irrigation water typically is delivered through a conduit to a water absorbent sheet of material, such as polypropylene felt By means of the natural absorbency of the material, the water is transported through the material to the growth medium of potted plants sitting on the absorbent material.

N-halohydantoin may be introduced into a greenhouse irrigation system by directing the stream of water to be used for irrigation through a brominator containing N-halohydantoin. The biocidal activity of the treated water not only tends to prevent development of unwanted microorganisms that otherwise Proliferate in the water and on the irrigation equipment, but also prevents the development of microorganisms that otherwise grow and Coat the irrigation mat and the Pots holding the plants. Thus, by including N-halohydantoin in the system, clogging of the irrigation equipment and coating of the irrigation mat are avoided, and the efficiency degradation normally encountered with the irrigation system is suppressed. Also extends the useful life cf the equipment. Further, such treatment of the irrigation water also inhibits development of microorganisms on the floor and other surfaces in the greenhouse often contacted by irrigation water run-off.

As for the plants themselves, the cleaner water provided by this method is believed to deliver to the plants via the roots thereof fewer living microorganisms that could be deleterious to the plant. Moreover, the biocidal activity of the treated water delivered to the plant is believed to inhibit microorganism development in and on the plant, and so helps prevent or control certain plant diseases which could result from Pathogenic microorganisms. Importantly, therefore, this method is believed to control diseases that otherwise spread quickly through the plants in a greenhouse. Also prevents spread of disease by re-cycled greenhouse irrigation water. Yet, despite such biocidal activity of water treated with N-halohydantoin, the Plant itself is not harmed by the treated water. Thus, irrigation water can be treated with N-halohydantoin for all these Purposes, to avoid fouling and clogging of the equipment and other surfaces and to treat the irrigated plants, without endangering the plant.

Walls, ceilings and floors in greenhouses, and even filters from evaporative coolers may be cleaned in accordance with this invention by hosing down the surfaces with treated water. The biocidally treated water kills the algae and other microorganisms that develop on the surfaces and cleans far more effectively than does untreated water, but treated water that splashes onto the Plants in the greenhouses does not harm the Plants as do other biocides such as bleach. Therefore very time consuming removal of plants from the greenhouse before cleaning is unnecessary. For this application, the water can be treated by dissolving N-halohydantoin in a volume of water, by inserting N-halohydantoin in the water stream, or by directing the stream, or a side stream, through a brominator containing N-halohydantoin. The greenhouse may then be quickly and easily hosed down without serious danger of harming the plants hit by splashed water, deflected water, extraneous atomized sprays of water, or even misdirected streams of water.

By the method of this invention, evaporative coolers or humidifiers, whether located in a greenhouse or another environment containing Plants, animals, or other organisms also can be maintained substantially free of fouling microorganisms without harming Plants or animals nearby. As with the other particular applications, N-halohydantoin can by incorporated at essentially any point in the system. Advantageously, N-halohydantoin can be Placed in a mesh bag in the water collecting well of the circulating system. The self-regulating mechanism of N-halohydantoin discussed above tends to maintain the treated water at an appropriate concentration. In accordance with this method, the evaporative pad remains substantially free of unwanted microorganisms that otherwise accumulate, while equipment, plants or other organisms contacted by atomized treated water drifting from the cooler or humidifier not only are not harmed by the treated water, but may be disinfected by the treated water. Thus, an unhealthy environment can be converted to a healthful, somewhat antiseptic environment.

As with greenhouse plants, crops or plants in an outdoor nursery may be irrigated with treated water. N-halohydantoin may be incorporated anywhere in the water system as described above, and the plants irrigated with the treated water by any, of several irrigation methods, such as spray irrigation, trickle or drip irrigation, mist or fog irrigation, sub-irrigation, ebb-and-flow irrigation, and hydroponics. Also as with the greenhouse irrigation methods, the treated water acts to control unwanted microorganisms from developing on the irrigation equipment, as well as in or on the Plants and growth medium in which the plants are rooted. The treatment thereby helps prevent certain Plant diseases arising from pathogenic microorganisms and control the outbreak and spread of such diseases.

In an alternative application of the method of the invention, solid N-halohydantoin may be Placed on or in the ground near growing plants so that rain or irrigation water delivers the N-halohydantoin to the plant's roots or rhizosphere. Likewise, solid N-halohydantoin may be placed on or in the ground near implanted bulbs or seeds so that rain or irrigation water delivers the N-halohydantoin to the roots or rhizosphere of plants grown from the bulbs or seeds. Or, if desired, the bulbs or seeds themselves may be treated by applying powder or granular N-halohydantoin or a slurry or solution of N-halohydantoin directly to the bulbs or seeds before planting.

In still another alternative embodiment of the application of the method of this invention growing plants may be treated with the treated water or by foliar application of an N-halohydantoin Powder, slurry or solution to inhibit the development of unwanted microorganisms and diseases on or in the fruit or seeds of the treated plants, and to delay rotting or spoiling of the Plants, fruit or seeds even after harvesting. Significantly, the treatment process of this invention not only is harmless to the plants, but because ingestion of N-halohydantoins in ordinary doses is widely believed to be safe to humans, unlike many presently available herbicides and pesticides, the resulting low doses of N-halohydantoin in the harvested plants, fruits and seeds appear to pose no appreciable health hazards to humans consuming them.

Due to the self-regulating quality, N-halohydantoin can also be applied to growing plants by Placing solid N-halohydantoin on or in the ground near the rhizosphere of plants, and rain water or irrigation water will dissolve the N-halohydantoin to the Plants in appropriate dosages. If desired, the N-halohydantoin can be applied to the ground before germination of seeds or growth of bulbs, and can even be applied to the ground while planting seeds or bulbs, thereby eliminating the need for a separate treatment step. Optionally, or in the alternative, N-halohydantoin can be added as a powder or slurry directly to bulbs or seeds before planting. It is believed that these applications of N-halohydantoin directly to the growth medium or the bulb or seed itself and transportation to the plant by rain or irrigation water is effective in controlling development of unwanted microorganisms and Plant diseases without harming higher order plants.

Alternatively, or additionally, N-halohydantoin can be applied topically to Plants, fruit or seeds after harvesting. The N-halohydantoin can be dissolved in water to form a treatment solution. Then, the harvested plants, fruit or seeds can be sprayed or washed with the treatment solution. Or, if so desired, the harvested plants, fruit or seeds can be dusted or coated with N-halohydantoin powder or an N-halohydantoin slurry. Regardless, the harvested plants, fruit and seeds are not harmed nor are they believed toxic to humans. Yet, microorganism development in and on the harvested Plants, fruit and seeds is inhibited and so rotting and spoiling is delayed.

Thus, N-halohydantoin can be applied in conjunction with irrigation, applied as a separate treatment or incorporated in water used for other purposes to protect plants unintentionally h t by the water.

Other advantages derived from the practice of this invention will become apparent from the following description and examples:

EXAMPLE 1

Experiments were conducted to compare the effectiveness of an N-halohydantoin composition with the effectiveness of sodium hypochlorite in producing desired levels of free residual halogen in infested water. A bromo-chloro-dimethylhydantoin (BCDMH) solution was calibrated so that five drops of the solution added to distilled water (300 ml) resulted in a solution of 1 ppm BCDMH. Water samples were collected from a muddy water see page area in a canal site. A second set of water samples was collected from a "swamp" at the bottom of an 800-foot well. The swamp water contained 0.5 ppm hydrogen sulfide, 0.8 ppm iron, 5 ppm aromatic hydroxyl compounds and probably other unknown impurities. Drops of the BCDMH solution were added to the water samples (300 ml each) and the free residual bromine in the sample measured to determine the BCDMH concentration necessary to Produce 0.6 Ppm free residual $Br^-$ in the sample. The results were compared to the sodium hypochlorite concentration necessary to Produce 0.6 ppm free residual $Cl^-$ in the sample. The $Cl^-$ concentration was measured with a standard Hach test kit. The $Br^-$ concentration was measured with a similar test kit. The results were as follows:

|  | Canal Water | Swamp Water |
| --- | --- | --- |
| Total NaOCl Added | 5.6 ppm | 4.2 ppm |
| Free Residual $Cl^-$ | 0.6 ppm | 0.6 ppm |
| Total BCDMH Added | 4.0 ppm | 3.4 ppm |
| Free Residual $Br^-$ | 0.6 ppm | 0.6 ppm |

Thus, about 23% to 40% more sodium hypochlorite than BCDMH was required to produce the same level of free residual halogen.

EXAMPLE 2

Chrysanthemums and gladioli were planted in four 50-foot plots under full-bed culture in EauGallie fine sand. The plants were irrigated by drip irrigation. One week later, BCDMH was introduced into the irrigation water of two of the 50-foot plots. The BCDMH was introduced to the irrigation water by mixing 9% aqueous BCDMH mixture (71 gal.) with water (4000 gal.). The 4071 gallons of total solution were applied to the two 50-foot plots (about 11 acre inches of irrigation) over almost ten weeks. Residual $Br^-$ concentration in the water collected from the end of the drip tube during operation was 2 to 2.5 ppm The following results, showing no adverse effect on either chrysanthemum or gladiolus production, were obtained:

|  | Chrysanthemums | |
| --- | --- | --- |
|  | Weight/Plant (lbs.) | No. of Plants |
| Untreated Plot | 3.6 | 100 |
| Treated Plot | 3.8 | 100 |
|  | Gladiolus | |
|  | No. of Stems | No. of Florets Per Stem |
| Untreated Plot | 55 | 14.2 |
| Treated Plot | 49 | 14.6 |

No significant difference in microorganism development was apparent between the tubes carrying treated water and those carrying untreated water, but it is believed that the duration of the trial was too short for any significant difference to appear.

EXAMPLE 3

Two sets of Yellow Mandalay chrysanthemums (thirty plants per set were grown and irrigated by subirrigation mats. The plants were fertilized with six ounces of Osmocote Per cubic foot of growing medium. One set of Plants (control) was not treated with biocide. For the other set of plants (test), BCDMH was injected into the irrigation system at a rate of about 2 to 4 ppm. Bromine levels of the test and control mats were measured daily and the bromine level was maintain 2 to 4 ppm higher than the level of the control. About eleven weeks after Planting, leaf samples were collected and analyzed. Table 1 shows levels (in percent by weight) of various nutrients (nutrients for which the fertilizer was the only direct Supply) found in the leaves and compared with desired levels):

While the test samples showed lower concentrations of some nutrients, the experiments were not conducted for such analysis and fertilization was not controlled. Thus, these results are not believed significant in distinguishing the effects of BCDMH on nutrient uptake. The plants were then evaluated for phytotoxicity. There was no observable phytotoxicity. The plant heights were measured, but no difference was observed between the heights or growth between the treated plants and the control plants.

While considerable algae growth had developed on the mat and fungus gnats had become a problem in the control set, there was no algae growth on the treated mat. Three weeks later, algae growth still had not appeared on the treated mat.

The experiment was repeated with exacum instead of chrysanthemums. Table 2 shows results from the foliar analysis were obtained:

TABLE 1

|         | N    | P    | K   | Ca  | Mg   | Mn  | Fe  | B   | Cu  | Zn  | Al  | Na  |
|---------|------|------|-----|-----|------|-----|-----|-----|-----|-----|-----|-----|
| Control | 3.42 | 0.23 | 4.1 | 2.2 | 0.64 | 339 | 111 | 20  | 7.7 | 181 | 34  | 25  |
| Test    | 3.32 | 0.12 | 1.6 | 1.0 | 0.39 | 208 | 54  | 11  | 4.6 | 126 | 22  | 21  |
| Desired | 4.5  | 0.4  | 4.0 | 1.0 | 0.3  | 30+ | 30+ | 30  | 5.0 | 30+ | —   | —   |

TABLE 2

|         | N    | P    | K    | Ca   | Mg   | Mn  | Fe   | B    | Cu  | Zn   | Al   | Na   |
|---------|------|------|------|------|------|-----|------|------|-----|------|------|------|
| Control | 4.32 | 0.30 | 1.21 | 0.75 | 0.69 | 229 | 87.9 | 39   | 4.7 | 49.7 | 20.9 | 8626 |
| Test    | 4.24 | 0.37 | 0.89 | 0.83 | 0.80 | 222 | 92.7 | 47.6 | 5.1 | 70.6 | 23.1 | 9376 |
| Desired | 4.5  | 0.4  | 4.0  | 1.0  | 0.3  | 30+ | 30+  | 30   | 5.0 | 30+  | —    | —    |

While the test samples showed lower concentrations of some nutrients, the experiments were not conducted for such analysis and fertilization was not controlled. Thus, these results are not believed significant in distinguishing the effects of BCDMH on nutrient uptake. Moreover, with the exacum it was noticed that of the 80 plants on the control mat, 50 had roots growing into the mat. Of the remaining 30 plants, many had roots growing out of the Pot, but not yet into the mat. However, of the 77 Plants on the treated mat, none "stuck" to the mat or had roots growing out of the bottom of the Pot. This avoidance of sticking to the mat is desirable for aesthetics and ease of handling.

EXAMPLE 4

The following Plants received a drench of foliar application of a saturated (1500 Ppm) BCDMH solution:

| Foliage Crop      | Potted Plants     |
|-------------------|-------------------|
| Pilea             | Grape Ivy         |
| Syngonium         | Zebra Plant       |
| Schefflera        | Velvet Plant      |
| Pepperomia        | English Ivy       |
| Dieffenbachia     | Christmas Cactus  |
| Ficus Benjamina   | Asparagus Fern    |
| Neanthe Bella     | Perrywinkle       |
| Maranta Leuconeura| Fibrous Begonia   |
|                   | Coleous           |
|                   | Impatiens         |

Applications were intermittent for three to six weeks in a greenhouse environment. No phytotoxicity was observed. In a separate experiment, the same types of plants received foliar sprays containing 1500 ppm BCDMH. Plants received 3 applications of spray separated by 10 day intervals. No phytotoxicity was observed.

The following plants were sprayed with BCDMH solutions of 1, 10, 100 and 1000 ppm in the spring:

| Potted Plants    | Flats              |
|------------------|--------------------|
| 8" Zonal Geranium| Fibrous Begonia    |
| 3" Tomatoes      | Seed Geranium      |
| 6" Pot Mums      | Non-Stop Begonias  |
| 4" Gebera        | Petunias           |
|                  | Impatiens          |

Except for occasional pinpoint burns on some flowers sprayed with the most concentrated solution, no other signs of phytotoxicity were observed. Undissolved articles of BCDMH are believed to have caused the pinpoint burns. Unopened buds were not harmed.

The following plants in 4-inch Pots were sprayed with BCDMH solutions of 1, 10, 100 and 1000 ppm in the summer:

| Potted Plants    |
|------------------|
| Pteris Cretica   |
| Gloxinia         |
| African Violet   |
| Gerbera          |
| Non-Stop Begonia |

Mild phytotoxicity symptoms were observed on open flowers at 100 and 1000 ppm.

EXAMPLE 5

Seeds were Planted in several Plots. Several sets of seeds were coated with various powder compositions. Some of the compositions comprised the commercially available products phygon, the dichlone 2,3-dichloro- 1,4-naphthoquinone, which is a trade designation of Uniroyal, and Vitavax, a carboxin, which is a trade designation of Uniroyal. The formulas of these Products are not known. One set of seeds in each plot were uncoated. The coatings for each set and the amounts of the coating (in ounces per hundred weight) were as follows:

| Set | Coating Composition | Amount of Coating |
|---|---|---|
| 1 | none | — |
| 2 | Pentachloronitrobenzene | 12 |
| 3 | Phygon 27X | 12 |
| 4 | Phygon 27X and Vitavax 30C | 10 and 3.3, resp. |
| 5 | Phygon 27 and Vitavax 30C | 10 and 3.3, resp. |
| 6 | Phygon 29 and Vitavax 30C | 10 and 3.3, resp. |
| 7 | Phygon 27 | 7 |
| 8 | Phygon 27 and Vitavax 30C | 7 and 3.3, resp. |
| 9 | Phygon 29 | 7 |
| 10 | Phygon 29 and Vitavax 30C | 7 and 3.3, resp. |
| 11 | Particulate 92.5% BCDMH | 5 |
| 12 | Particulate 92.5% BCDMH | 10 |

The seeds were planted in various plots, with the following survival rates (in percent of planted seeds that survived) of the seeds (sets 11 and 12 were planted only in plot 3):

| | Plots | | | | | |
|---|---|---|---|---|---|---|
| Set | 1 | 2 | 3 | 4 | 5 | 6 |
| 1 | 83 | 34 | 43 | 77 | 25 | 59 |
| 2 | 76 | 31 | 58 | 77 | 28 | 61 |
| 3 | 81 | 34 | 63 | 79 | 26 | 64 |
| 4 | 82 | 26 | 69 | 73 | 48 | 63 |
| 5 | 83 | 30 | 60 | 79 | 39 | 63 |
| 6 | 82 | 41 | 55 | 80 | 43 | 65 |
| 7 | 78 | 33 | 41 | 80 | — | 58 |
| 8 | 82 | 39 | 58 | 81 | — | 65 |
| 9 | 80 | 37 | 46 | 77 | — | 60 |
| 10 | 83 | 32 | 60 | 81 | — | 64 |
| 11 | — | — | 47 | — | — | — |
| 12 | — | — | 58 | — | — | — |
| Minimum significant differences | 5 | — | 11 | — | 11 | — |

The minimum significant difference indicates the 95% confidence range within which there is no significant difference. For example, for the survival rate of set 12 (58%), there is no significant difference between survival rates between 47% and 69%. Thus, it appears from the data that the BCDMH seed coating is at least as effective as the other coatings.

In view of the above, it will be seen that the several objects of the invention are achieved and other advantageous results attained.

What is claimed is:

1. A method for controlling disease caused by microorganisms or growth of unwanted microorganisms in or on a growing higher order plant without harming the plant, the method comprising:
   providing contact, in the presence of water, between an N-halohydantoin and the plant, the rhizosphere of the plant, or a grwoth medium in which a seed or bulb for the plant is planted, the N-halohydantoin being selected from the group consisting of a 1-bromo-3-chloro-5,5-dialkyl-hydantoin and a 1,3-dibromo-5,5-dialkylhydantoin, and being provided in an amount sufficient to control said disease or microorganisms.

2. A method as set forth in claim 1 wherein higher order plants are irrigated and treated for control of diseases caused by microorganisms or growth of microorqanisms, the method includinq the steps of:
   incorporating N-halohydantoin in water to produce treated water having a concentration of N-halohydantoin sufficient to inhibit the growth of microorganisms; and
   irrigating said higher order plants with the treated water.

3. A method as set forth in claim 2 wherein the plants are irrigated by means of spray irrigation.

4. A method as set forth in claim 2 wherein the concentration of N-halohydantoin is between about 1 ppm and and about 1500 ppm by weight.

5. A method as set forth in claim 4 wherein the N-halohydantoin concentration is between about 2 ppm and about 10 ppm by weight.

6. A method as set forth in claim 5 wherein the N-halohydantoin concentration is between about 5 ppm and about 10 ppm by weight.

7. A method as set forth in claim 2 wherein the N-halohydantoin comprises an N-halogenated dimethylhydantoin.

8. A method as set forth in claim 7 wherein the N-halohydantoin comprises 1-bromo-3-chloro-5,5-dimethylhydantoin.

9. A method as forth in claim 7 wherein the N-halohydantoin comprises I, 3-dibromo-5,5-dimethylhydantoin.

10. A method as set forth in claim 2 wherein higher order plants are irrigated by transportation of water to the plants by water absorbent material, the method including the steps of:
    arranging the plants and the water-absorbent material so that water may be transported through the water-absorbent material and contact the plants are growth medium in which they or rooted;
    incorporating N-halohydantoin in water to produce treated water having a concentration of N-halohydantoin sufficient to inhibit the growth of microorganisms; and
    delivering said treated water to said water absorbent material, thereby effecting transport of treated water to said plants or said growth medium.

11. A method as set forth in claim 1 wherein an N-halohydantoin is applied to a growth medium in which the plant is rooted, the N-halohydantoin being dissolved in, and conveyed to said rhizosphere by precipitation or irrigation water received by said growth medium.

12. A method as set forth in claim 11 wherein the N-halohydantoin comprises an N-halogenated dimethylhydantoin.

13. A method as set forth in claim 12 wherein the N-halohydantoin comprises I-bromo-3-chloro-5,5-dimethylhydantoin.

14. A method as set forth in claim 12 wherein said N-halohydantoin comprises 1,3-dibromo-5,5-dimethylhydantoin.

15. A method as set forth in claim 1 wherein higher order plants are harvested, the method including:
    contacting growing higher order plants with an N-halohydantoin; and
    harvesting said growing plants to collect harvested plants, whereby rotting or spoiling of the, harvested plants is inhibited.

16. A method as set forth in claim 1 wherein higher order plants are treated with N-halohydantoin and harvested fruit or seeds are produced from the treated plants, the method including the steps of:

contacting growing higher order plants bearing fruit or seeds with an N-halohydantoin;

harvesting fruit or seeds from said higher order plants to collect harvested fruit or seeds, whereby rotting or spoiling of the harvested fruit or seeds is inhibited.

17. A method as set forth in claim 16 wherein the growing plants are contacted with the N-halohydantoin by:

dissolving the N-halohydantoin in water to produce a disinfectant solution having a concentration of N-halohydantoin sufficient to inhibit growth of microorganisms; and contacting the growing plants bearing fruit or seeds with the disinfectant solution.

18. A method as set forth in 17 wherein the plants are contacted with the disinfectant solution by applying the disinfectant solution as irrigation water to the growing plants.

19. A method as set forth in claim 17 wherein the concentration of N-halohydantoin is between about 1 ppm to about 1500 ppm by weight.

20. A method as set forth in claim 19 wherein the N-halohydantoin concentration is between about 2 ppm and about 10 ppm by weight.

21. A method as set forth in claim 20 wherein the N-halohydantoin concentration is between about 5 ppm and about 10 ppm by weight.

22. A method as set forth in claim 17 wherein the N-halohydantoin comprises an N-halogenated dimethylhydantoin.

23. A method as set forth in claim 22 wherein the N-halohydantoin comprises 1-bromo-3-chloro-5,5-dimethylhydantoin.

24. A method as set forth in claim 22 wherein the N-halohydantoin comprises 1,3-dibromo-5,5-dimethylhydantoin.

25. A method as set forth in claim 1 wherein the N-halohydantoin is applied to a growth medium in which a seed or bulb for the plant is implanted, the N-halohydantoin being dissolved in and conveyed by precipitation or irrigation water received by said growth medium to said seed, bulb, or plant resulting from germination of said seed or bulb.

26. A method as set forth in claim 25 wher-in the N-halohydantoin comprises an N-halogenated dimethylhydantoin.

27. A method as set forth in claim 26 wherein said N-halohydantoin comprises 1-bromo-3-chloro-5,5-dimethylhydantoin.

28. A method as set forth in claim 26 wherein the N-halohydantoin comprises 1,3-dibromo-5,5-dimethyl hydantoin.

* * * * *

UNITED STATES PATENT AND TRADEMARK OFFICE
CERTIFICATE OF CORRECTION

PATENT NO. : 4,925,866

DATED : May 15, 1990

INVENTOR(S) : Roger E. Smith

It is certified that error appears in the above-identified patent and that said Letters Patent is hereby corrected as shown below:

In the title of the cover page, "Microoganisms", should read ---Microorganisms---.

Column 13, line 60, "grwoth", should read ---growth---.

Column 14, lines1-2, "microorqanisms", should read ---microorganisms---.

Column 14, line 2, "includinq", should read ---including---.

Column 14, line 27, "comprises I", should read ---comprises 1---.

Column 14, line 53, "I-bromo", should read ---1-bromo---.

Column 16, line 20, "wher-in", should read ---wherein---.

Signed and Sealed this

Nineteenth Day of November, 1991

*Attest:*

HARRY F. MANBECK, JR.

*Attesting Officer*      *Commissioner of Patents and Trademarks*